(12) United States Patent
Takaku et al.

(10) Patent No.: US 7,354,950 B2
(45) Date of Patent: Apr. 8, 2008

(54) 1,3-DIOXANE DERIVATIVES, COMPOSITION, OPTICAL ELEMENT AND DISPLAY DEVICE CONTAINING THE SAME

(75) Inventors: Koji Takaku, Kanagawa (JP); Akihide Osaku, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/708,606

(22) Filed: Feb. 21, 2007

(65) Prior Publication Data

US 2007/0194278 A1 Aug. 23, 2007

(30) Foreign Application Priority Data

Feb. 23, 2006 (JP) ............................. 2006-046801

(51) Int. Cl.
*A61K 31/357* (2006.01)
*C07D 319/06* (2006.01)
*C09K 19/00* (2006.01)

(52) U.S. Cl. .................... 514/452; 549/375; 252/299.1

(58) Field of Classification Search ................ 514/452; 549/375; 252/299.1
See application file for complete search history.

(56) References Cited

U.S. PATENT DOCUMENTS 4,313,878 A  2/1982  Hsu

*Primary Examiner*—Taofiq Solola
(74) *Attorney, Agent, or Firm*—Birch, Stewart, Kolasch & Birch, LLP

(57) ABSTRACT

A composition includes at least one compound represented by the following Formula (1). In the Formula (1), $R^1$ represents an alkyl group having 1 to 18 carbon atoms, $R^2$ represents a hydrogen atom or a substituent, and $R^3$ represents a substituent, m represents an integer of from 0 to 4, and n represents an integer of from 1 to 5.

Formula (1)

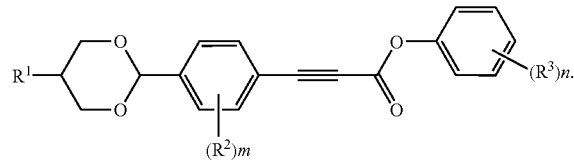

18 Claims, No Drawings

1,3-DIOXANE DERIVATIVES, COMPOSITION, OPTICAL ELEMENT AND DISPLAY DEVICE CONTAINING THE SAME

CROSS REFERENCE TO RELATED APPLICATION

This application claims priority under 35USC 119 from Japanese Patent Application No. 2006-046801, the disclosure of which is incorporated by reference herein.

BACKGROUND OF THE INVENTION

1. Field of the Invention

The invention relates to a 1,3-dioxane derivative, particularly a 1,3-dioxane derivative which may be suitable for a liquid crystal compound, a liquid crystal composition and a display device; a composition and a display device containing the same.

2. Description of the Related Art

Liquid crystals (liquid crystal compounds) have been widely used in devices such as displays, optical elements such as retardation films and other applications, but the development of new materials suitable for these objects have been desired. Demands for liquid crystal materials include a reduction of a threshold voltage and an increase of a contrast.

A threshold voltage (Vth) is, as represented by the following formula, a function of dielectric anisotropy ($\Delta\epsilon$) (refer to Mol. Cryst. Liq. Cryst., 12, 57 (1970)).

$$Vth = \pi\{K/(\epsilon_0 \times |\Delta\epsilon|)\}^{1/2}$$

In the above formula, K represents an elastic constant, and $\epsilon_0$ represents a dielectric constant in vacuum.

As shown in the formula, a threshold voltage (Vth) is decreased by increasing the absolute value of a dielectric anisotropy ($\Delta\epsilon$), and/or decreasing an elastic constant K. Accordingly, liquid crystalline compounds having a large dielectric anisotropy ($\Delta\epsilon$) have been intensively developed.

Under such circumstance, for example, a 1,3-dioxane derivative is disclosed as a liquid crystal material having a positive dielectric anisotropy in U.S. Pat. No. 4,313,878. For display devices such as devices such as LCD, development of liquid crystal materials which are superior to conventional liquid crystals in intended optical performance and others have been further desired.

SUMMARY OF THE INVENTION

A first aspect according to the present invention is a composition comprising at least one compound represented by the following Formula (1).

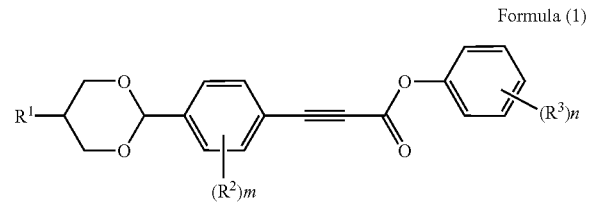

Formula (1)

In the Formula (1), $R^1$ represents an alkyl group having 1 to 18 carbon atoms, $R^2$ represents a hydrogen atom or a substituent, $R^3$ represents a substituent, m represents an integer of from 0 to 4, and n represents an integer of from 1 to 5.

A second aspect according to the present invention is a compound represented by the following Formula (1).

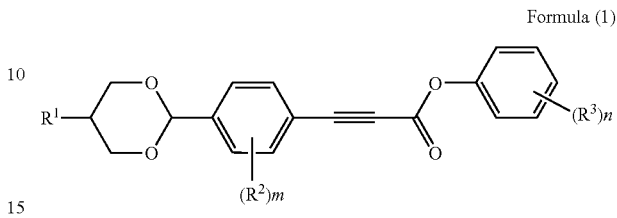

Formula (1)

In the Formula (1), $R^1$ represents an alkyl group having 1 to 18 carbon atoms, $R^2$ represents a hydrogen atom or a substituent, $R^3$ represents a substituent, m represents an integer of from 0 to 4, and n represents an integer of from 1 to 5.

A third aspect according to the present invention is a display device comprising a pair of electrode substrates and a liquid crystal layer disposed between the pair of electrode substrates, wherein the liquid crystal layer comprises at least one composition according to the first aspect.

A fourth aspect according to the present invention is a compound represented by the following Formula (2).

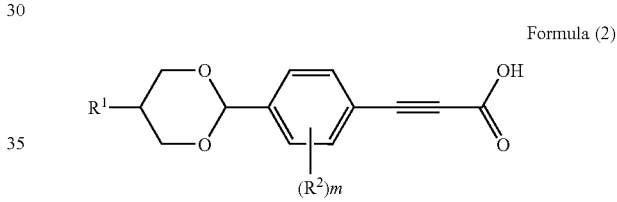

Formula (2)

In the Formula (2), $R^1$ represents an alkyl group having 1 to 18 carbon atoms, $R^2$ represents a hydrogen atom or a substituent, and m represents an integer of from 0 to 4.

A fifth aspect according to the present invention is an optical element containing at least one compound according to the first embodiment.

DETAILED DESCRIPTION OF THE PRESENT INVENTION

The present invention will be described in detail below. In the present specification " . . . to . . . " represents a range including the numeral values represented before and after "to" as a minimum value and a maximum value, respectively.

First, the relationship between the structure of the compound represented by Formula (1) (hereinafter referred to as "the compound according to the present invention" as appropriate) and dielectric anisotropy $\Delta\epsilon$ is described.

Dielectric anisotropy ($\Delta\epsilon$) indicates a difference between a dielectric constant which is parallel with the alignment of molecules and a dielectric constant which is perpendicular to the alignment of molecules, and is represented by the following formula.

Dielectric anisotropy ($\Delta\epsilon$) = $\epsilon_\parallel - \epsilon_\perp$ In the above formula, $\epsilon_\parallel$ represents a dielectric constant which is parallel with the alignment of molecules, and $\epsilon_\perp$ represents a dielectric constant which is perpendicular to the alignment of molecules. More specifically, for positively increasing the dielectric anisotropy (Δε), it is effective to increase the polarization in the long axis direction within the molecules of a rod-like liquid crystal compound, and for negatively increasing the dielectric anisotropy (Δε), it is effective to increase the polarization in the short axis direction.

The compound according to the present invention represented by the following Formula (1) is shown below.

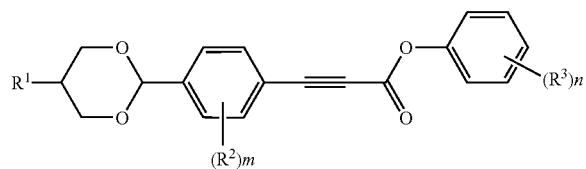

Formula (1)

In the Formula (1), $R^1$ represents an alkyl group having 1 to 18 carbon atoms, $R^2$ represents a hydrogen atom or a substituent, and $R^3$ represents a substituent, m represents an integer of from 0 to 4, and n represents an integer of from 1 to 5.

In the compound represented by Formula (1), a dipole of the 1,3-dioxane ring is oriented to a long axis direction of a molecule, and furthermore, an acetylene bond extends a conjugated system to increase the dielectric constant ε∥ in a long axis direction.

Furthermore, as shown below, in the compound represented by Formula (1), a presence of a carbonyl group in a ester group promotes a polarization in the short axis direction. As a result, the compound represented by Formula (1) is able to demonstrate a dual frequency addressing property in the range available for liquid crystal addressing. Specifically in the compound according to the present invention, an ester group is adjacent to an acetylene group, which increases the absolute value of the dielectric anisotropy at low and high frequencies. Accordingly, the compound is suitable as a dual frequency addressable liquid crystal.

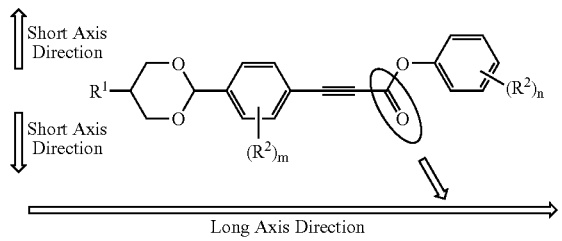

The compound represented by Formula (1) is further described in detail below.

The 1,3-dioxane ring in the Formula (1) may be in either cis or trans conformation, and preferably in trans conformation.

The benzene ring adjacent to the 1,3-dioxane ring is a benzene ring having binding sites at the 1 and 4 positions so as to increase the linearity of the rod-like compound.

Furthermore, as described above, in the compound according to the present invention represented by Formula (1), an acetylene group is adjacent to an ester group. In the compound, the 1,3-dioxane ring is not directly adjacent to the acetylene group in consideration of the stability of the compound.

$R^1$ in the Formula (1) is an alkyl group having 1 to 18 carbon atoms, preferably an alkyl group having 3 to 12 carbon atoms, and more preferably an alkyl group having 3 to 5 carbon atoms (e.g., n-propyl, n-butyl, and n-pentyl groups). Herein, the alkyl group refers to a straight chain or a branched alkyl group, and may have a substituent (a substituent group V as listed below) or unsubstituted. Furthermore, the alkyl group represented by $R^1$ may have an unsaturated bond such as 3-hexenyl group. Examples of the substituents include those listed in the substituent group V (Substituent Group V)

A halogen atom (e.g., chlorine, bromine, iodine, fluorine), a cyano group, an alkoxy group having 1 to 10 carbon atoms, preferably 1 to 8 carbon atoms, more preferably having 1 to 4 carbon atoms (e.g., methoxy, ethoxy, 2-methoxy ethoxy), an acyloxy group having 1 to 10 carbon atoms, preferably having 2 to 6 carbon atoms, and more preferably having 2 to 4 carbon atoms (e.g., acetyloxy), and an alkoxycarbonyl group having 2 to 10 carbon atoms, preferably having 2 to 6 carbon atoms, and more preferably having 2 to 4 carbon atoms (e.g., methoxycarbonyl and ethoxycarbonyl). Furthermore, these substituents may be further substituted thereon with one of the substituents as listed in the description of V.

$R^2$ in the Formula (1) represents a hydrogen atom or a substituent group as listed in the following substituent group W, preferably a hydrogen atom, an alkyl group, an alkenyl group, an alkynyl group, a cyano group, a fluorine atom, a chlorine atom, an isothiocyanate group, an alkoxy group, an alkoxycarbonyl group, or an acyloxy group, and more preferably, a hydrogen atom, an alkyl group, a cyano group, a fluorine atom, or a chlorine atom.

(Substituent Group W)

A halogen atom (e.g., chlorine, bromine, iodine, and fluorine), a mercapto group, a cyano group, a carboxyl group, a phosphate group, a sulfo group, a carbamoyl group having 1 to 10 carbon atoms, preferably having 2 to 8 carbon atoms, and more preferably having 2 to 5 carbon atoms (e.g., methylcarbamoyl, ethylcarbamoyl, and morpholinocarbamoyl), a sulfamoyl group having 0 to 10 carbon atoms, preferably having 2 to 8 carbon atoms, and more preferably having 2 to 5 carbon atoms (e.g., methylsulfamoyl, ethylsulfamoyl, and piperidinosulfamoyl), a nitro group, an alkoxy group having 1 to 20 carbon atoms, preferably having 1 to 10 carbon atoms, and more preferably having 1 to 8 carbon atoms (e.g., methoxy, ethoxy, 2-methoxyethoxy, and 2-phenylethoxy), an aryloxy group having 6 to 20 carbon atoms, preferably having 6 to 12 carbon atoms, and more preferably having 6 to 10 carbon atoms (e.g., phenoxy, p-methylphenoxy, p-chlorophenoxy, and naphthoxy), an acyl group having 1 to 20 carbon atoms, preferably having 2 to 12 carbon atoms, and more preferably having 2 to 8 carbon atoms (e.g., acetyl, benzoyl, and trichloroacetyl), an acyloxy group having 1 to 20 carbon atoms, preferably having 2 to 12 carbon atoms, and more preferably having 2 to 8 carbon atoms (e.g., acetyloxy and benzoyloxy), an acylamino group having 1 to 20 carbon atoms, preferably having 2 to 12 carbon atoms, and more preferably having 2 to 8 carbon atoms (e.g., acetylamino), a sulfonyl group having 1 to 20 carbon atoms, preferably having 1 to 10 carbon atoms, and more preferably having 1 to 8 carbon atoms (e.g., methanesulfonyl, ethanesulfonyl, and benzenesulfonyl), a sulfinyl group having 1 to 20 carbon atoms, preferably having 1 to 10 carbon atoms, and more preferably having 1 to 8 carbon atoms (e.g., methanesulfinyl, ethanesulfinyl, and benzenesulfinyl), a substituted or unsubstituted amino group having 1 to 20 carbon atoms, preferably having 1 to 12 carbon atoms, and more preferably having 1 to 8 carbon atoms (e.g., amino, methylamino, dimethylamino, benzylamino, anilino, diphenylamino, 4-methylphenylamino, 4-ethylphenylamino, 3-n-propylphenylamino, 4-n-propylphenylamino, 3-n-butylphenylamino, 4-n-butylphenylamino, 3-n-pentylphenylamino, 4-n-pentylphenylamino, 3-trifluoromethylphenylamino, 4-trifluoromethylphenylamino, 2-pyridylamino, 3-pyridylamino, 2-thiazolylamino, 2-oxazolylamino, N,N-methylphenylamino, and N,N-ethylphenylamino), an ammonium group having 0 to 15 carbon atoms, preferably having 3 to 10 carbon atoms, and more preferably having 3 to 6 carbon atoms (e.g., trimethyl ammonium and triethyl ammonium), a hydrazino group having 0 to 15 carbon atoms, preferably having 1 to 10 carbon atoms, and more preferably having 1 to 6 carbon atoms (e.g., trimethylhydrazino group), an ureido group having 1 to 15 carbon atoms, preferably having 1 to 10 carbon atoms, and more preferably having 1 to 6 carbon atoms (e.g., ureido group, and N,N-dimethyl ureido group), an imide group having 1 to 15 carbon atoms, preferably having 1 to 10 carbon atoms, and more preferably having 1 to 6 carbon atoms (e.g., succinimide group), an alkylthio group having 1 to 20 carbon atoms, preferably having 1 to 12 carbon atoms, and more preferably having 1 to 8 carbon atoms (e.g., methylthio, ethylthio, and propylthio), an arylthio group having 6 to 80 carbon atoms, preferably having 6 to 40 carbon atoms, and more preferably having 6 to 30 carbon atoms (e.g., phenylthio, p-methylphenylthio, p-chlorophenylthio, 2-pyridylthio, 1-naphthylthio, 2-naphthylthio, 4-propylcyclohexyl-4'-biphenylthio, 4-butylcyclohexyl-4'-biphenylthio, 4-pentylcyclohexyl-4'-biphenylthio, and 4-propylphenyl-2-ethynyl-4'-biphenylthio), a heteroarylthio group having 1 to 80 carbon atoms, preferably having 1 to 40 carbon atoms, and more preferably having 1 to 30 carbon atoms (e.g., 2-pyridylthio, 3-pyridylthio, 4-pyridylthio, 2-quinolylthio, 2-furylthio, and 2-pyrrolylthio), an alkoxycarbonyl group having 2 to 20 carbon atoms, preferably having 2 to 12 carbon atoms, and more preferably having 2 to 8 carbon atoms (e.g., methoxycarbonyl, ethoxycarbonyl, and 2-benzyloxycarbonyl), an aryloxy carbonyl group having 6 to 20 carbon atoms, preferably having 6 to 12 carbon atoms, and more preferably having 6 to 10 carbon atoms (e.g., phenoxycarbonyl), an unsubstituted alkyl group having 1 to 18 carbon atoms, preferably having 1 to 10 carbon atoms, and more preferably having 1 to 5 carbon atoms (e.g., methyl, ethyl, propyl, and butyl), a substituted alkyl group having 1 to 18 carbon atoms, preferably having 1 to 10 carbon atoms, and more preferably having 1 to 5 carbon atoms {e.g., hydroxymethyl, trifluoromethyl, benzyl, carboxyethyl, ethoxycarbonylmethyl, and acetylaminomethyl; the substituted alkyl group includes an unsaturated hydrocarbon group having 2 to 18 carbon atoms, preferably having 3 to 10 carbon atoms, and more preferably having 3 to 5 carbon atoms (e.g., vinyl group, ethynyl group, 1-cyclohexenyl group, benzylidyne group, and benzylidene group)}, a substituted or unsubstituted aryl group having 6 to 20 carbon atoms, preferably having 6 to 15 carbon atoms, and more preferably having 6 to 10 carbon atoms (e.g., phenyl, naphthyl, p-carboxyphenyl, p-nitrophenyl, 3,5-dichlorophenyl, p-cyanophenyl, m-fluorophenyl, p-tolyl, 4-propyl cyclohexyl-4'-biphenyl, 4-butylcyclohexyl-4'-biphenyl, 4-pentylcyclohexyl-4'-biphenyl, and 4-propylphenyl-2-ethynyl-4'-biphenyl), and a substituted or unsubstituted heteroaryl group having 1 to 20 carbon atoms, preferably having 2 to 10 carbon atoms, and more preferably having 4 to 6 carbon atoms (e.g., pyridyl, 5-methylpyridyl, thienyl, furyl, morpholino, and tetrahydrofurfuryl).

The substituents as listed in the substituent group W may be condensed with a benzene ring or a naphthalene ring. Furthermore, these substituents may be further substituted thereon with one of the substituents as listed in the description of W.

When $R^2$ in the Formula (1) is an alkyl group, the alkyl group is equivalent to $R^1$, refers to a straight chain or a branched alkyl group, and may have a substituent or unsubstituted. Furthermore, the alkyl group represented by $R^2$ may have, for example, an unsaturated bond such as 3-hexenyl group.

$R^3$ in the Formula (1) represents a substituent as listed in the substituent group W, preferably, a cyano group, a fluorine atom, a chlorine atom, an isothiocyanate group, an alkoxy group, an alkoxycarbonyl group, an acyloxy group, an aryloxycarbonyl group, a carbamoyl group, an acylamino group, an alkylamino group, an alkyl group, an alkenyl group, an alkynyl group, or an aryl group, and more preferably, a cyano group, a fluorine atom, a chlorine atom, an isothiocyanate group, an alkoxy group, an alkoxycarbonyl group, an acyloxy group, or an aryl group.

Furthermore, $R^3$ in the Formula (1) may form a ring by further binding to the phenyl group to which $R^3$ binds. Examples of the ring formed by binding $R^3$ and a phenyl group include a naphthalene ring and a tetrahydronaphthalene ring.

In the Formula (1), m represents an integer of from 0 to 4, and preferably an integer of from 0 to 2.

In the Formula (1), n represents an integer of from 1 to 5, and preferably represents an integer of from 1 to 3.

Specific examples of the compound according to the present invention are listed below, but the present invention is not limited thereto.

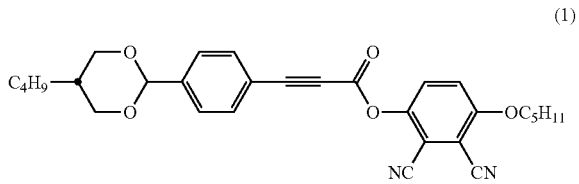

(1)

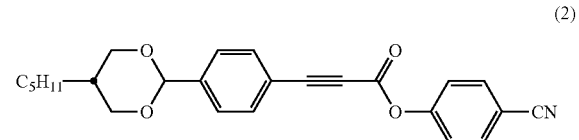

(2)

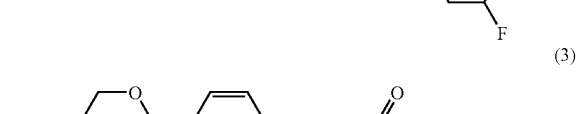

(3)

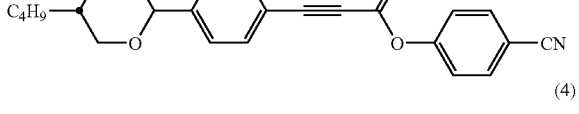

(4)

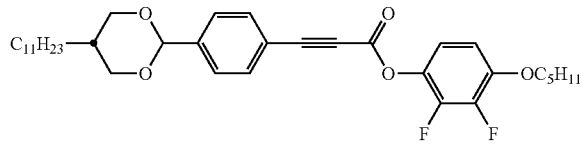

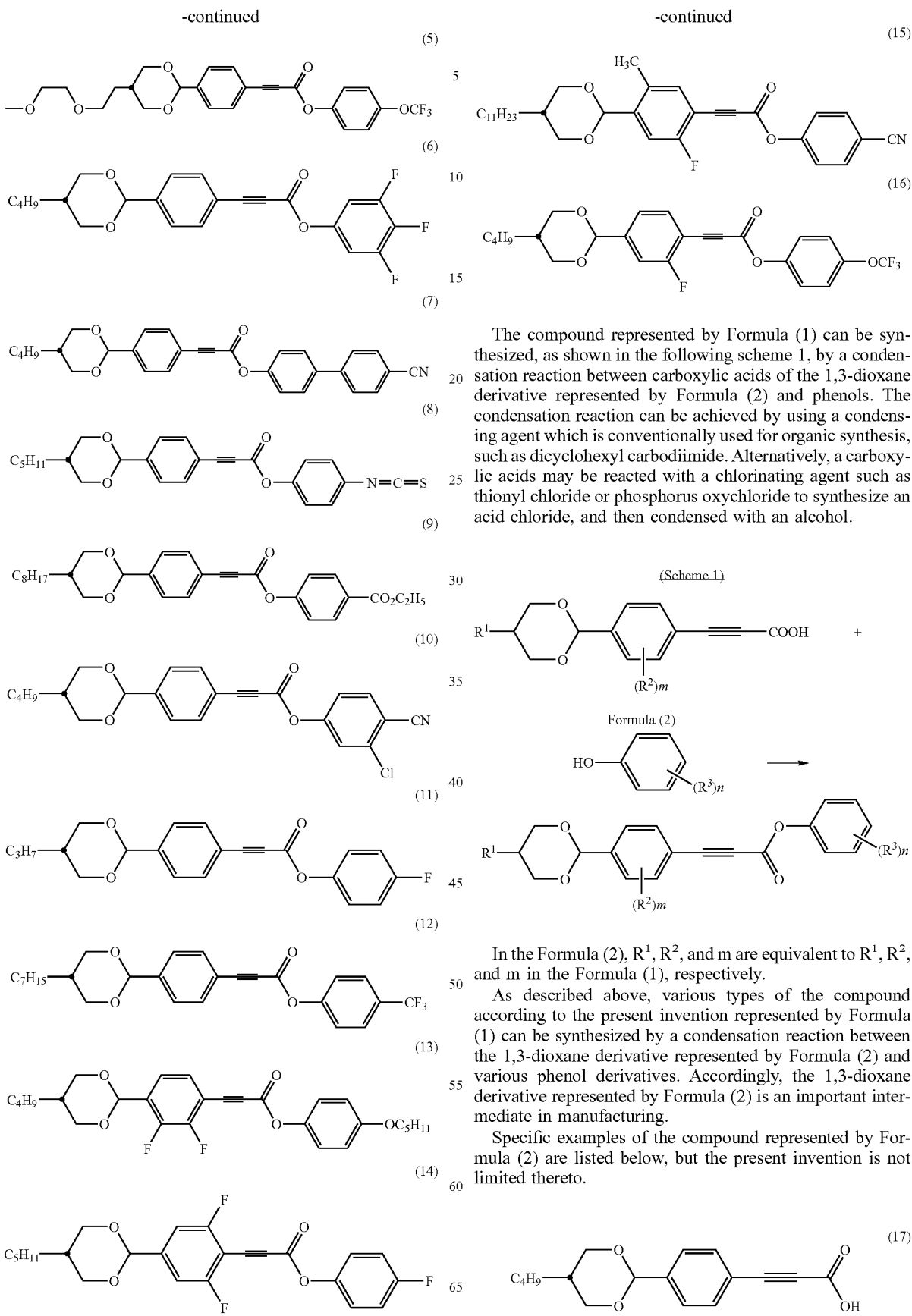

The compound represented by Formula (1) can be synthesized, as shown in the following scheme 1, by a condensation reaction between carboxylic acids of the 1,3-dioxane derivative represented by Formula (2) and phenols. The condensation reaction can be achieved by using a condensing agent which is conventionally used for organic synthesis, such as dicyclohexyl carbodiimide. Alternatively, a carboxylic acids may be reacted with a chlorinating agent such as thionyl chloride or phosphorus oxychloride to synthesize an acid chloride, and then condensed with an alcohol.

In the Formula (2), $R^1$, $R^2$, and m are equivalent to $R^1$, $R^2$, and m in the Formula (1), respectively.

As described above, various types of the compound according to the present invention represented by Formula (1) can be synthesized by a condensation reaction between the 1,3-dioxane derivative represented by Formula (2) and various phenol derivatives. Accordingly, the 1,3-dioxane derivative represented by Formula (2) is an important intermediate in manufacturing.

Specific examples of the compound represented by Formula (2) are listed below, but the present invention is not limited thereto.

-continued

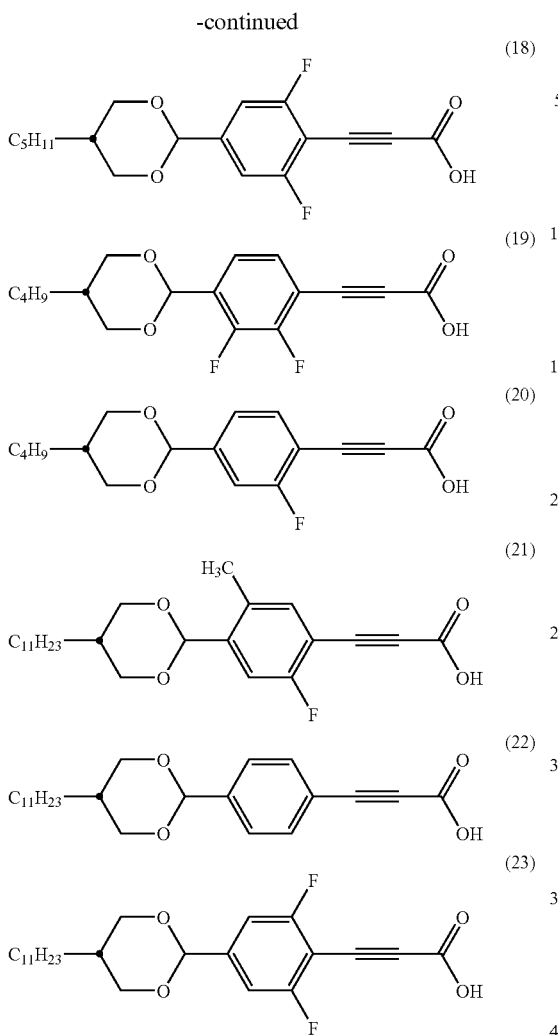

The carboxylic acid, which is the 1,3-dioxane derivative represented by Formula (2), can be synthesized, as represented by the following scheme 2, by dehydration condensation reaction between a corresponding 1,3-diol compound and an aromatic aldehyde having an ethynyl group under the presence of an acid catalyst, followed by a reaction with carbon dioxide using n-butyl lithium.

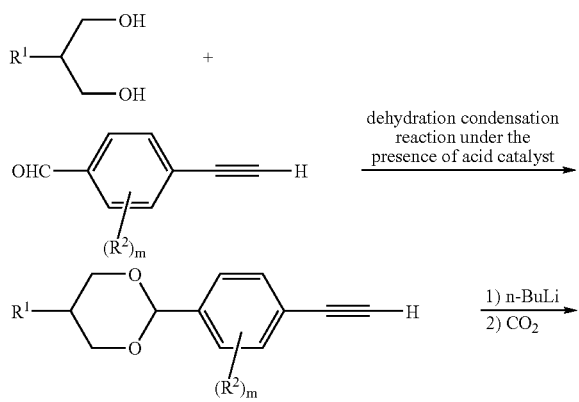

-continued

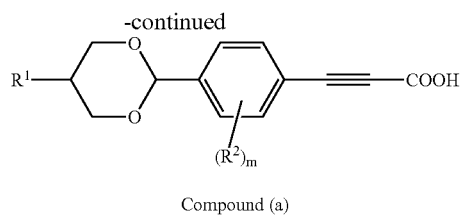

Compound (a)

The present invention provides a composition which contains at least one type of the compound represented by Formula (1). The composition may contain one or two or more types of the compound represented by Formula (1), or, as appropriate, may be mixed with a known liquid crystal compound or the like to be used as a liquid crystal composition (preferably a guest host-type liquid crystal composition). When the composition according to the present invention is used as a liquid crystal composition, the physical properties (e.g., optical property) of the composition may be controlled as appropriate using a liquid crystal to be mixed with.

In the composition according to the present invention, compatible liquid crystal compounds are not particularly limited, but dual frequency addressable liquid crystal compounds (nematic and smectic) are preferable, and the following dual frequency addressable nematic liquid crystal (H-1) as described in Applied Physics Letters, Vol. 25, 186-188 (1974) is more preferable.

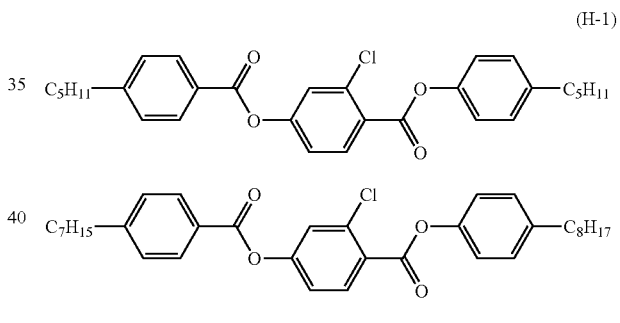

(1:1 mixture)

The liquid crystal demonstrating a dual frequency addressing property means a liquid crystal which has a positive dielectric anisotropy when the frequency of an electric field applied to the liquid crystal is in a low frequency region, and the sign of the dielectric anisotropy becomes negative when the frequency is in a high frequency region. Detailed descriptions as to the liquid crystal are given in the pages of 189 to 192 of "Liquid crystal device handbook" (edited by the 142nd Committee in Japan Society for the Promotion of Science, Nikkan Kogyo Shimbun, Ltd., 1989).

The compound and/or composition according to the present invention can be used in a display device (e.g., liquid crystal display). For example, the display device has a pair of electrode substrates and a liquid crystal layer disposed between the pair of electrode substrates, and the liquid crystal layer includes at least one type of the compound according to the present invention.

The compound and/or the composition according to the present invention can be preferably used as an optical element described below. The optical element in the present invention refers to, specifically, a functional film such as a circularly polarized light-emitting film, an optical film, a retardation film, a ferroelectric film, an antiferroelectric film, and a piezoelectric film; and a functional element such as a (circularly) polarized light-emitting device, a laser oscillation device excited by light or an electric field (based on a primary photonic effect), an LCD backlight, a non-linear optical device, an electro-optical device, a pyroelectric element, a piezoelectric element, or a light modulation element.

The optical element according to the present invention can be manufactured by, for example:

(1) a method of applying the compound (or composition) according to the present invention to a sheet of support or a pair of supports (e.g., cells), followed by crosslinking; or (2) a method of injecting the compound (or composition) according to the present invention into the support(s) without being processed.

The compound according to the present invention represented by Formula (1) has a large dielectric anisotropy, thus display devices or optical elements using the compound according to the present invention have low threshold voltage. Therefore electric power consumption of the display devices or optical elements may be decreased by using the compound according to the present invention.

EXAMPLES

The present invention is further illustrated below by the following Examples. However, those Examples are for illustrative explanation of the present invention, and the present invention is not limited to them.

Example 1

(Synthesis of Compound 1)

The compound (1) was synthesized according to the following scheme.

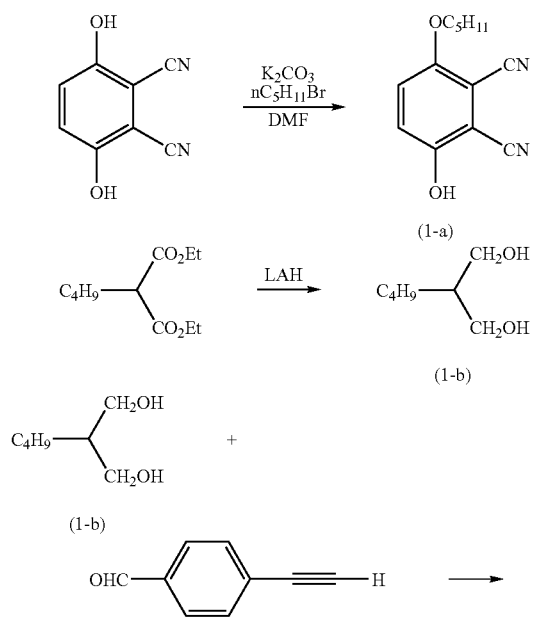

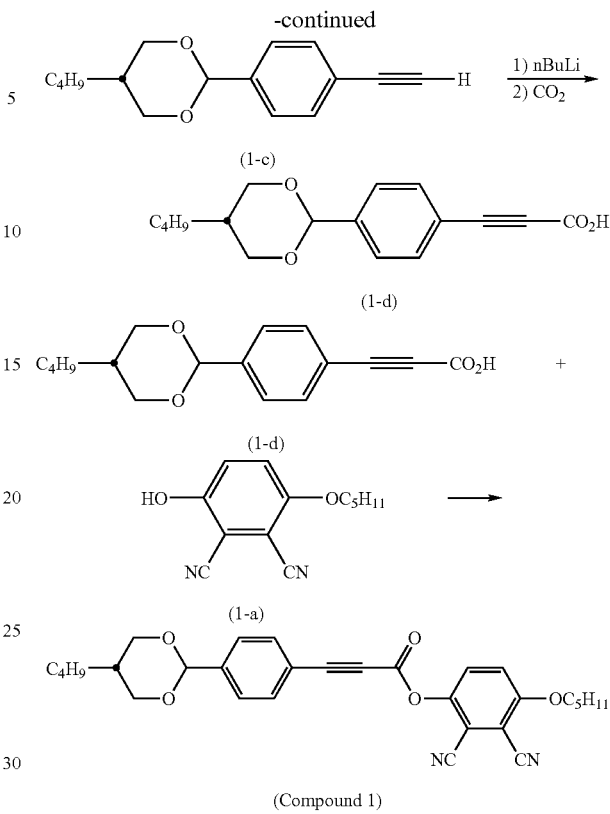

(Synthesis of Compound (1-a))

compound (1-a) was synthesized by using 2,3-dicyano-hydroquinone (manufactured by Wako Pure Chemical Industries, Ltd.) according to the synthesis method as described in Mol. Cryst. Liq. Cryst., 94, 109-118 (1983).

(Synthesis of Compound (1-b))

To 100 ml of a 1 M THF solution of lithium aluminum hydride (manufactured by Aldrich), 10 g of butyl malonate diethyl (manufactured by Wako Pure Chemical Industries, Ltd.) was added under cooling with ice, and stirred for 5 hours while heated under reflux. The reaction liquid was added into a 1 N aqueous hydrochloric acid under cooling with ice, stirred for 30 minutes, and extracted with ethyl acetate. The extract was dried over magnesium sulfate, and concentrated under reduced pressure to obtain 5.7 g of the compound (1-b).

(Synthesis of Compound (1-c))

To 20 ml of a chloroform solution of 1.3 g of the compound (1-b) and 1.3 g of 4-ethynyl benzaldehyde (manufactured by Aldrich), 0.2 g of AMVERLYST (R) 15H (manufactured by ICN Biomedicals, Inc) was added, and stirred for 5 hours while heated under reflux. The reaction liquid was filtered, and the filtrate was concentrated under reduced pressure. The concentration residue was purified through silica gel column chromatography (developing solvent: ethyl acetate/hexane=1/5) to obtain 2.1 g of the compound (1-c).

(Synthesis of Compound (1-d))

To 30 ml of a THF solution containing 2.2 g of the compound (1-c), 6.8 ml of a 1.6 M hexane solution containing n-butyl lithium was added dropwise at −78° C., stirred for 3 hours, and further stirred for 1 hour while carbon dioxide was bubbled through the liquid. The reaction liquid was added to ethyl acetate/1 N aqueous hydrochloric. The organic layer was rinsed with a 1 N aqueous hydrochloric acid, dried over magnesium sulfate, and concentrated under reduced pressure to obtain 2.2 g of the compound (1-d).

$^1$H-NMR (CDCl$_3$)

δ: 0.88 (3H, t), 0.99-1.17 (2H, m), 1.19-1.38 (4H, m), 2.02-2.18 (1H, m), 3.52 (2H, t), 4.23 (2H, dd), 5.42 (1H, s), 7.52 (2H, d), 7.60 (2H, d), 13 or more (1H, bs)

(Synthesis of Liquid Crystal Compound 1)

To 10 ml a methylene chloride solution which contains 200 mg of the compound (1-d) and 160 mg of the compound (1-a), 5 ml of a methylene chloride solution containing 172 mg of dicyclohexyl carbodiimide was added dropwise, and stirred for 1 hour under cooling with ice. The reaction liquid was added to ethyl acetate/water. The organic layer was dried over magnesium sulfate, and concentrated under reduced pressure. The concentration residue was purified through silica gel column chromatography (developing solvent: ethyl acetate/hexane=1/2) to obtain 310 mg of the liquid crystal compound (1). The compound was identified by elementary analysis, NMR, and MASS spectrum. The appearance was a white solid.

The transition temperature of the obtained liquid crystal compound (1) was measured by observation with polarizing microscope (manufactured by Nikon Corporation) while the temperature was changed with a hot stage (manufactured by TOYO Corporation) and by DSC.

Transition temperature: Cr 128 (SmC 74 N 100) Iso

The dielectric anisotropy Δε of the obtained liquid crystal compound (1) was calculated by an extrapolation method using a liquid crystal (trade name: MLC-6608, manufactured by Merck Ltd.).

Δε(100 Hz)=+0.2,

Δε(30 kHz)=−15.4

$^1$H-NMR (CDCl$_3$)

δ: 0.92 (3H, t), 0.96 (3H, t), 1.05-1.17 (2H, m), 1.22-1.56 (7H, m), 1.81-1.95 (2H, m), 2.02-2.22 (2H, m), 3.55 (2H, t), 4.12 (2H, dd), 4.26 (2H, dd), 5.43 (1H, s), 7.23 (1H, d), 7.52 (1H, d), 7.56 (2H, d), 7.66 (2H, d)

Example 2

(Synthesis of Liquid Crystal Compound 3)

The liquid crystal compound 3 was obtained by the same synthesis method as the liquid crystal compound 1, except that the compound (1-a) was replaced with 4-cyanophenol.

The transition temperature and dielectric anisotropy of the obtained liquid crystal compound 3 were measured by the same method as Example 1.

Transition temperature: Cr 84 N 191 Iso

Dielectric anisotropy Δε:

Δε(100 Hz)=40.1

Δε(25 kHz)=−5.4

$^1$H-NMR (CDCl$_3$)

δ: 0.90 (3H, t), 1.05-1.17 (2H, m), 1.22-1.39 (4H, m), 2.04-2.19 (1H, m), 3.54 (2H, t), 4.24 (2H, dd), 5.42 (1H, s), 7.33 (2H, d), 7.55 (2H, d), 7.64 (2H, d), 7.72 (2H, d)

The liquid crystal compound 1 and liquid crystal compound 3 have a large dielectric anisotropy at low and high frequencies, indicating that the compounds are preferable as a dual frequency addressable liquid crystal.

Example 3

(Synthesis of Liquid Crystal Compound 3)

The liquid crystal compounds 5, 6, 11 and 14 were obtained by the same synthesis method as the liquid crystal compound 1. The dielectric anisotropies Δε of the obtained compounds were calculated by the same method as Example 1. The results were shown in Table 1.

TABLE 1

| Compound | Low Frequency (100 Hz) | High Frequency (25 kHz) |
| --- | --- | --- |
| 5 | 28.5 | −4.7 |
| 6 | 25.7 | −5.8 |
| 11 | 14.6 | −4.9 |
| 14 | 27.3 | −6.2 |

The compounds according to the present invention have a large dielectric anisotropy at low and high frequencies, indicating that the compounds are preferable as a dual frequency addressable liquid crystal.

Example 4

82 mg of the dual frequency addressable nematic liquid crystal (H-1) described in Applied Physics Letters, Vol. 25, 186-188 (1974) and 18 mg of the liquid crystal compound 1 according to the present invention were mixed, and then heated at 180° C. for one hour by hot plate. After the mixture was cooled to room temperature, it was left to stand at room temperature for one day to obtain the composition 1.

Example 5

80 mg of the dual frequency addressable nematic liquid crystal (H-1) of Example 4 and 20 mg of the liquid crystal compound 3 of Example 3 were mixed, and then heated at 180° C. for one hour by hot plate. After the mixture was cooled to room temperature, it was left to stand at room temperature for one day to obtain the composition 2.

Example 6

The dielectric anisotropies (Δε) of the compositions obtained by Examples 4 and 5 were measured by dielectric substance measuring apparatus (Trade name: Solartron 1255B, 1296; manufactured by TOYO Corporation). The results were shown in Table 2.

TABLE 2

| | Δε (100 Hz) | Δε (25 Hz) | Remarks |
| --- | --- | --- | --- |
| H-1 | 5.58 | −2.21 | Comparative Example |
| Composition 1 | 4.61 | −4.58 | Present Invention |
| Composition 2 | 12.48 | −2.85 | Present Invention |

The liquid crystal composition 1 has a larger negative dielectric anisotropy at high frequencies (25 kHz) than the comparative compound H-1, and the liquid crystal composition 2 has a larger negative and positive dielectric anisotropy at low (10 Hz) and high (25 kHz) frequencies respectively than the comparative compound H-1, indicating that the compounds are preferable as a dual frequency addressable liquid crystal.

The foregoing description of the embodiments of the present invention has been provided for the purposes of illustration and description. It is not intended to be exhaustive or to limit the present invention to the precise forms disclosed. Obviously, many modifications and variations will be apparent to practitioners skilled in the art. The embodiments were chosen and described in order to best explain the principles of the present invention and its practical applications, thereby enabling others skilled in the art to understand the present invention for various embodiments and with the various modifications as are suited to the particular use contemplated. It is intended that the scope of the present invention be defined by the following claims and their equivalents.

All publications, patent applications, and technical standards mentioned in this specification are herein incorporated by reference to the same extent as if each individual publication, patent application, or technical standard was specifically and individually indicated to be incorporated by reference.

What is claimed is:

1. A composition comprising at least one compound represented by the following Formula (1):

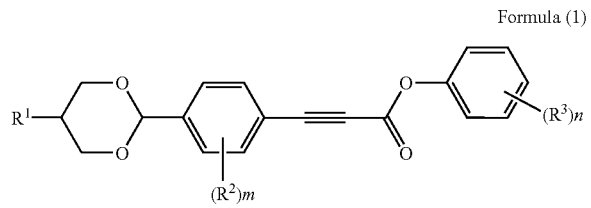

Formula (1)

wherein in Formula (1), $R^1$ represents an alkyl group having 1 to 18 carbon atoms, $R^2$ represents a hydrogen atom or a substituent, $R^3$ represents a substituent, m represents an integer of from 0 to 4, and n represents an integer of from 1 to 5.

2. The composition according to claim 1, wherein $R^1$ in the Formula (1) represents an alkyl group having 3 to 12 carbon atoms; $R^2$ represents a hydrogen atom, a halogen atom, an alkyl group, or a cyano group; and $R^3$ is a cyano group, a fluorine atom, a chlorine atom, an isothiocyanate group, an alkoxy group, an alkoxycarbonyl group, an acyloxy group, an aryloxycarbonyl group, a carbamoyl group, an acylamino group, an alkylamino group, an alkyl group, an alkenyl group, an alkynyl group or an aryl group.

3. The composition according to claim 1, wherein $R^1$ in the Formula (1) represents an alkyl group having 3 to 5 carbon atoms.

4. The composition according to claim 1, wherein $R^2$ in the Formula (1) represents a hydrogen atom or a halogen atom.

5. The composition according to claim 1, wherein $R^3$ in the Formula (1) represents a cyano group, a fluorine atom, a chlorine atom, an isothiocyanate group, an alkoxy group, an alkoxycarbonyl group, an acyloxy group or an aryl group.

6. The composition according to claim 1, wherein m in the Formula (1) is from 0 to 2.

7. The composition according to claim 1, wherein n in the Formula (1) is from 1 to 3.

8. A compound represented by the following Formula (1):

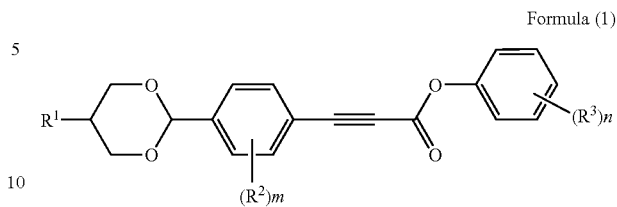

Formula (1)

wherein in Formula (1), $R^1$ represents an alkyl group having 1 to 18 carbon atoms, $R^2$ represents a hydrogen atom or a substituent, $R^3$ represents a substituent, m represents an integer of from 0 to 4, and n represents an integer of from 1 to 5.

9. A display device comprising a pair of electrode substrates and a liquid crystal layer disposed between the pair of electrode substrates, wherein the liquid crystal layer comprises at least one composition according to claim 1.

10. A compound represented by the following Formula (2):

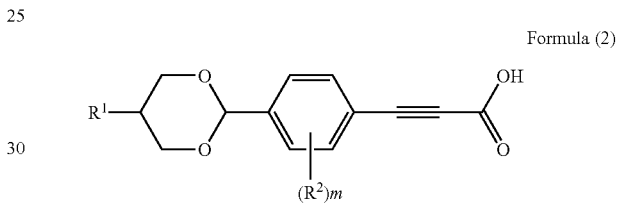

Formula (2)

wherein in the Formula (2), $R^1$ represents an alkyl group having 1 to 18 carbon atoms, $R^2$ represents a hydrogen atom or a substituent, and m represents an integer of from 0 to 4.

11. The compound according to claim 10, wherein $R^1$ in the Formula (2) represents an alkyl group having 3 to 5 carbon atoms.

12. The compound according to claim 10, wherein $R^2$ in the Formula (2) represents a hydrogen atom or a halogen atom.

13. The compound according to claim 1, wherein m in the Formula (2) is from 0 to 2.

14. An optical element containing at least the composition according to claim 1.

15. An optical element comprising the composition according to claim 1 as a dual frequency addressable liquid crystal.

16. The optical element according to claim 14, wherein the optical element is used as a functional film or a functional element.

17. The optical element according to claim 16, wherein the functional film is a circularly polarized light-emitting film, an optical film, a retardation film, a ferroelectric film, an antiferroelectric film or a piezoelectric film.

18. The optical element according to claim 16, wherein the functional element is a polarizing light-emitting device, a laser oscillation device excited by light or an electric field, an LCD backlight, a non-linear optical device, an electro-optical device, a pyroelectric element, a piezoelectric element or a light modulation element.

* * * * *